United States Patent
Smith et al.

(10) Patent No.: US 8,803,475 B2
(45) Date of Patent: *Aug. 12, 2014

(54) SURGICAL STERILIZER WITH INTEGRATED BATTERY CHARGING DEVICE

(71) Applicant: Syntheon, LLC, Miami, FL (US)

(72) Inventors: Kevin W. Smith, Coral Gables, FL (US); Sean M. McBrayer, Miami, FL (US); Derek Dee Deville, Coral Gables, FL (US); Thomas O. Bales, Jr., Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/682,261

(22) Filed: Nov. 20, 2012

(65) Prior Publication Data

US 2013/0076307 A1  Mar. 28, 2013

Related U.S. Application Data

(62) Division of application No. 12/878,508, filed on Sep. 9, 2010, now Pat. No. 8,278,873, and a division of application No. 12/879,651, filed on Sep. 10, 2010, now Pat. No. 8,344,690, and a division of application No. 13/110,213, filed on May 18, 2011, now Pat. No. 8,344,691.

(51) Int. Cl.
*H02J 7/00* (2006.01)

(52) U.S. Cl.
USPC .......................................... 320/108; 320/113

(58) Field of Classification Search
USPC .......................................... 320/103, 108, 113
See application file for complete search history.

(56) References Cited

U.S. PATENT DOCUMENTS

| | | | |
|---|---|---|---|
| 4,068,643 A | 1/1978 | McKechnie | |
| 4,288,733 A * | 9/1981 | Bilanceri et al. | 320/113 |
| 4,641,076 A * | 2/1987 | Linden | 320/113 |
| 4,996,128 A | 2/1991 | Aldecoa | |
| 5,399,007 A * | 3/1995 | Marconet | 312/209 |
| 6,096,264 A * | 8/2000 | Peifer | 422/1 |
| 6,666,875 B1 | 12/2003 | Sakurai et al. | |
| 6,847,190 B2 * | 1/2005 | Schaefer et al. | 320/107 |
| 6,919,183 B2 * | 7/2005 | Fandl et al. | 435/7.2 |
| 7,622,892 B2 * | 11/2009 | Kim et al. | 320/108 |
| 8,258,745 B2 * | 9/2012 | Smith et al. | 320/108 |

(Continued)

FOREIGN PATENT DOCUMENTS

JP  2000287987  10/2000

*Primary Examiner* — Richard V Muralidar
(74) *Attorney, Agent, or Firm* — Mayback & Hoffman, P.A.; Gregory L. Mayback; Rebecca A. Tie

(57) ABSTRACT

A device for sterilizing and charging a battery of an instrument, comprising a sterilization device sealingly enclosing therein at least one battery of an instrument and operable to sterilize the at least one battery, an inductively powered battery-charging device disposed inside the sterilization device and having a charger operable to be placed in conductive contact with and charge the at least one battery and a power receiver sub-assembly electrically coupled to the charger and operable to receive electrical power inductively from outside the sterilization device and supply the received electrical power to the charger to charge the battery during sterilization, and a power supply disposed outside the sterilization device and operable to supply power inductively to the power receiver sub-assembly through the sterilization device.

18 Claims, 2 Drawing Sheets

(56) References Cited

U.S. PATENT DOCUMENTS

| | | | |
|---|---|---|---|
| 8,278,873 B2 * | 10/2012 | Smith et al. | 320/108 |
| 8,344,690 B2 * | 1/2013 | Smith et al. | 320/108 |
| 8,344,691 B2 * | 1/2013 | Smith et al. | 320/108 |
| 2006/0069403 A1 | 3/2006 | Shalon et al. | |
| 2008/0175761 A1 | 7/2008 | Thur et al. | |
| 2010/0076455 A1 * | 3/2010 | Birkenbach et al. | 606/130 |
| 2011/0057608 A1 | 3/2011 | Smith | |
| 2011/0057609 A1 | 3/2011 | Smith | |
| 2011/0227529 A1 | 9/2011 | Smith | |
| 2013/0043834 A1 * | 2/2013 | Smith et al. | 320/108 |

* cited by examiner

SURGICAL STERILIZER WITH INTEGRATED BATTERY CHARGING DEVICE

CROSS-REFERENCE TO RELATED APPLICATIONS

This application is a divisional application of:

U.S. patent application Ser. No. 12/878,508, now U.S. Pat. No. 8,278,873, filed on Sep. 9, 2010, and U.S. patent application Ser. No. 12/879,651, now U.S. Pat. No. 8,344,690, filed on Sep. 10, 2010 (these applications both claiming the priority, under 35 U.S.C. §119, of U.S. Provisional Patent Application Ser. No. 61/241,328, filed on Sep. 10, 2009); and U.S. patent application Ser. No. 13/110,213, now U.S. Pat. No. 8,344,691, filed on May 18, 2011 (wherein U.S. patent application Ser. No. 13/087,644, now U.S. Pat. No. 8,258,745, filed on Apr. 15, 2011, is a continuation in part of U.S. patent application Ser. Nos. 12/878,508 and 12/879,651; and U.S. patent application Ser. No. 13/557,607, filed on Jul. 25, 2012, is a divisional application of U.S. patent application Ser. No. 13/087,644 and a continuation in part of U.S. patent application Ser. Nos. 12/878,508, 12/879,651, and 13/110,213), the entire disclosures of which are hereby incorporated herein by reference in their entireties.

FIELD OF INVENTION

The present invention lies in the field of surgical sterilization devices and methods for the sterilization of surgical instruments. The present disclosure relates specifically to a surgical sterilizer with an integrated battery charging device and a method for surgical sterilization while charging a battery, the battery being used in a battery-powered medical instrument or with a device used in surgical procedures. The surgical sterilization and the simultaneous charging of the battery occurs without compromising the sterile field by either the act of sterilizing or the act of charging the battery.

BACKGROUND OF THE INVENTION

A unique set of problems arise when a sterilized surgical device or medical instrument also has a removable battery component that needs to periodically removed from the device and recharged. Such battery components do not stay within the sterile field of a singular operation as they are intended to be used for multiple and different surgical procedures on different patients. As such, to reduce the risk of spreading disease and infection, the battery must be sterilized before it can be reused in another surgical procedure. If the battery component is not sterilized prior to being connected to a sterile recharging device, then there is a risk that any contaminants on the battery will spread to the recharging device once the non-sterile battery is connected. If the battery is sterilized prior to being connected to the recharging device, then there is a risk that any contaminants existing on a non-sterile recharging device will spread to the battery. Therefore, it becomes necessary to use more than one sterilization cycle to maintain a sterile environment, which can be costly, time-consuming and harmful to the integrity of the battery.

If the battery is not sterilized at all and is removed from and inserted into the device without contaminating the sterile field by successfully implementing aseptic transfer techniques that are known in the art, there still remains a risk that the recharging device will be exposed to any contaminants on the non-sterile battery, or vice versa, and serve as a source for spreading disease and infection. Accordingly, it would be desirable to be able to sterilize objects including a rechargeable battery while simultaneously charging it so that the sterility of the battery is not compromised by the act of charging the battery and so that the battery can be quickly recharged and sterilized in one stage, thereby returning the battery to use as quickly as possible.

There are existing prior art devices that recharge the battery components inside surgical instruments while maintaining the already pre-existing sterile nature of the surgical instruments during the time that the instrument is being recharged. For example, in U.S. Pat. No. 6,666,875 to Sakurai et al., an apparatus is described that recharges a surgical instrument that has already been sterilized such that the apparatus maintains the pre-existing sterile nature of the instrument while it is being recharged. The Sakurai et al. apparatus includes a surgical instrument, such as an ultrasonic knife, and a recharger. The recharger is plugged into an electrical mains and an alternating current is supplied to an output circuit that is connected to a power transmission circuit that includes a power transmission coil. Electromagnetic energy is radiated outwards from the power transmission coil and into the surroundings. The surgical instrument has an internal rechargeable secondary battery and a power reception unit that includes a power reception coil that is wound about the battery chamber. To recharge the Sakurai et al. instrument, electromagnetic energy is induced in the power reception coil of the power reception unit by the power transmission coil of the recharger. A rectification control unit converts the electromagnetic energy received by the power reception unit into direct current and adjusts the voltage to a level suitable for recharging the secondary battery. Accordingly, electromagnetic energy is radiated outwards from the power transmission coil and into the surroundings and is received by the power reception coil in the secondary battery without requiring any physical contact between the surgical instrument and the recharger. To maintain the sterile nature of the surgical instrument, the recharger has a separate sealed, sterilized container (for example, a vial) formed on the top of the recharger for holding the already sterilized surgical instrument while it is being recharged. This separate container must be transparent to electromagnetic energy so that the electromagnetic energy being radiated outward from the recharger may be transmitted through the container and to the power reception coil in the secondary battery of the instrument. The container must be watertight and capable of being washed and disinfected.

However, because these devices do not function to actively sterilize the instruments and only serve to maintain the pre-existing sterile nature of the instruments, a costly and time-consuming two-stage process is still required to reintroduce the instrument into a sterile, surgical environment. The instrument must be sterilized in one stage and recharged in a separate, second stage while in a sterile environment. In addition, the sealed, sterile container used to hold the instrument while it is being charged must be cleaned and disinfected prior to and after each time that it is used. Furthermore, there is no reliable and fail-safe indication on the container itself as to whether or not it has been cleaned and disinfected prior to being used. As a result, there is still a risk that the sterile nature of the instrument will be compromised. Thus, it would be beneficial to have a sterilizing device that not only sterilizes a removable, rechargeable battery of a surgical instrument but also recharges the battery simultaneously to ensure that the battery is both recharged and sterilized successfully in a single stage and in the same environment.

In the prior art, there does exist one or more devices that simultaneously sterilize and recharge personal articles having battery components in a single stage. For example, in U.S. Pat. No. 6,096,264 to Peifer, a device is described that is used to store, sterilize, and recharge electric toothbrushes. The device is comprised of a cabinet that includes a housing that encloses an internal sterilizing chamber. The internal sterilizing chamber has a microbe-destroying agent inside, such as a sterilizing lamp that emits ultraviolet (UV) radiation. A holder is mounted inside the chamber and is comprised of a plurality of receptacles that receive and support the toothbrushes. Each receptacle has associated recharging elements for recharging the toothbrush that is associated with the receptacle. The recharging elements include pairs of exposed contacts and covered induction coils. A plug and a power cord extend outside of the housing for connection to a domestic receptacle. Power from the cord is connected to an AC/DC converter, which, in turn, is connected to the contacts and coils of the receptacles. Accordingly, the battery components of the toothbrushes are inductively charged using the induction coils on the exposed contacts of the receptacles and simultaneously, the toothbrushes are sterilized.

However, this device, as well as others, requires that the sterile chamber or housing be breached so that a power cord can be drawn into the chamber or housing so that power can be provided to the electrical contacts on the recharging elements. Therefore, only a certain degree of sterility can be created or maintained by these devices, which, while it may be suitable for personal articles such as toothbrushes, it is not sufficient in view of operating room standards (as legally mandated by regulatory agencies) and for valid sterilization of surgical instruments, referred to herein as "surgical sterilization." Also, and similarly to the device described in Sakurai et al. and other devices like it, this device sterilizes the toothbrush or the instrument itself and not the battery inside the toothbrush or instrument. Therefore, a non-sterile component is still present in the device even after the sterilization procedure has been completed. Accordingly, it would be desirable to have a device that simultaneously sterilizes and recharges a battery, whereby a power cord or other method of drawing power into the sterilization chamber does not breach the surgical sterilization chamber and therefore, is capable of sterilizing surgical instruments and the like, and directly recharges the battery.

In addition, the receptacles described in the Peifer device for receiving and supporting the toothbrushes so that the toothbrushes can be recharged necessarily cover a portion of the toothbrushes and shield the covered portion and the electrical contacts from the UV radiation that sterilizes the toothbrush. Therefore, a portion of the toothbrush and the recharging elements of the device are not adequately exposed to the UV radiation and, therefore, are not sufficiently sterilized. Accordingly, it would be desirable to have a device that simultaneously sterilizes and recharges a battery that does not require obscuring a portion of the battery, the surgical instrument, or the recharging elements of the device from the sterilizing components or agents.

It would also be advantageous to be able to adapt or retrofit existing (and, most likely, expensive) surgical sterilizing systems with the capability of simultaneously recharging a battery to be sterilized thereby allowing a surgeon or other operating room personnel to continue to use any conventional or standard sterilization system rather than requiring replacement of the conventional or standard systems. As a result, the large expense and training time that would be required to overhaul the existing sterilization systems would be avoided entirely. None of the devices described in the prior art, however, disclose such an ability to recharge a sterilizable battery in an existing sterilization system.

Thus, a need exists to overcome the problems with the prior art as discussed above.

SUMMARY OF THE INVENTION

Embodiments of the present invention provide a device for sterilizing and charging a battery of an instrument, comprising a sterilization device sealingly enclosing therein at least one battery of an instrument and operable to sterilize the at least one battery, an inductively powered battery-charging device disposed inside the sterilization device and having a charger operable to be placed in conductive contact with and charge the at least one battery and a power receiver sub-assembly electrically coupled to the charger and operable to receive electrical power inductively from outside the sterilization device and supply the received electrical power to the charger to charge the battery during sterilization, and a power supply disposed outside the sterilization device and operable to supply power inductively to the power receiver sub-assembly through the sterilization device.

With the objects of the invention in view, there is also provided a device for sterilizing and charging a battery of an instrument, comprising a sterilization device sealingly enclosing therein at least one battery of an instrument and operable to sterilize the at least one battery, an inductively powered battery-charging device disposed inside the sterilization device and having a charger operable to be placed in conductive contact with and charge the at least one battery, a power receiver sub-assembly electrically coupled to the charger and operable to receive electrical power inductively from outside the sterilization device and supply the received electrical power to the charger to charge the battery during sterilization, and a power supply disposed outside the sterilization device and having an inductive power supply sub-assembly operable to supply power inductively to the power receiver sub-assembly through the sterilization device and an electric mains supply operable to supply power to the inductive power supply sub-assembly, whereby the inductive power supply sub-assembly and the power receiver sub-assembly together forming an inductive charging assembly.

In accordance with another feature of the present invention, the charger includes at least one electrical contact shaped to conductively contact at least one corresponding electrical battery contact of the battery.

In accordance with another feature of the present invention, the inductive power supply sub-assembly is comprised of a first magnetic inductive coil disposed outside the sterilization device and having a primary winding electrically coupled to the electric mains supply and the power receiver sub-assembly is comprised of a second magnetic inductive coil disposed within the sterilization device and having a secondary winding electrically coupled to the charger, the second magnetic inductive coil being adjacent to and substantially aligned with the first magnetic inductive coil such that the first magnetic inductive coil induces an electrical current in the second magnetic inductive coil when the electric mains supply powers the first magnetic inductive coil.

In accordance with yet another feature of the present invention, the inductive charging assembly does not breach the sterilization device.

In accordance with yet another feature of the present invention, the sterilization device is comprised of a material that permits transmission of electromagnetic waves therethrough.

In accordance with a further feature of the present invention, the sterilization device is operable to surgically sterilize the at least one battery using at least one of temperature of at least 100 degrees Celsius, a chemical agent, and radiation.

In accordance with yet another feature of the present invention, the first and second magnetic inductive coils each have a magnetic core.

In accordance with yet another feature, the first and second magnetic inductive coils each have a ferrite core.

In accordance with another feature, an embodiment of the present invention further comprises an alignment component operable to substantially align the first and second magnetic inductive coils on either side of the sterilization device.

In accordance with a further feature of the present invention, the alignment component is comprised of at least one first magnet of the first magnetic inductive coil and at least one second magnet of the second magnetic inductive coil having magnetically opposite poles.

In accordance with another feature, an embodiment of the present invention further comprises a sealed container operable to enclose the at least one battery to create a microbial seal around the at least one battery and to permit charging of the at least one battery while enclosing the at least one battery in the microbial seal.

With the objects of the invention in view, there is further provided a device for sterilizing and charging a battery of an instrument, comprising a sterilization device sealingly enclosing therein at least one battery of an instrument and operable to sterilize the at least one battery and an inductively powered battery-charging device disposed inside the sterilization device and in conductive contact with the at least one battery such that it is operable to charge the battery during sterilization and operable to inductively receive power from a power source located outside of the sterilization device such that the sterilization device is not breached.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims. The construction and method of operation of the invention, however, together with additional objects and advantages thereof, will be best understood from the following description of specific embodiments when read in connection with the accompanying drawings.

Although the invention is illustrated and described herein as embodied in a surgical sterilizer with an integrated battery charging device and a method for surgical sterilization while charging a battery, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION OF THE INVENTION

Figure 1:
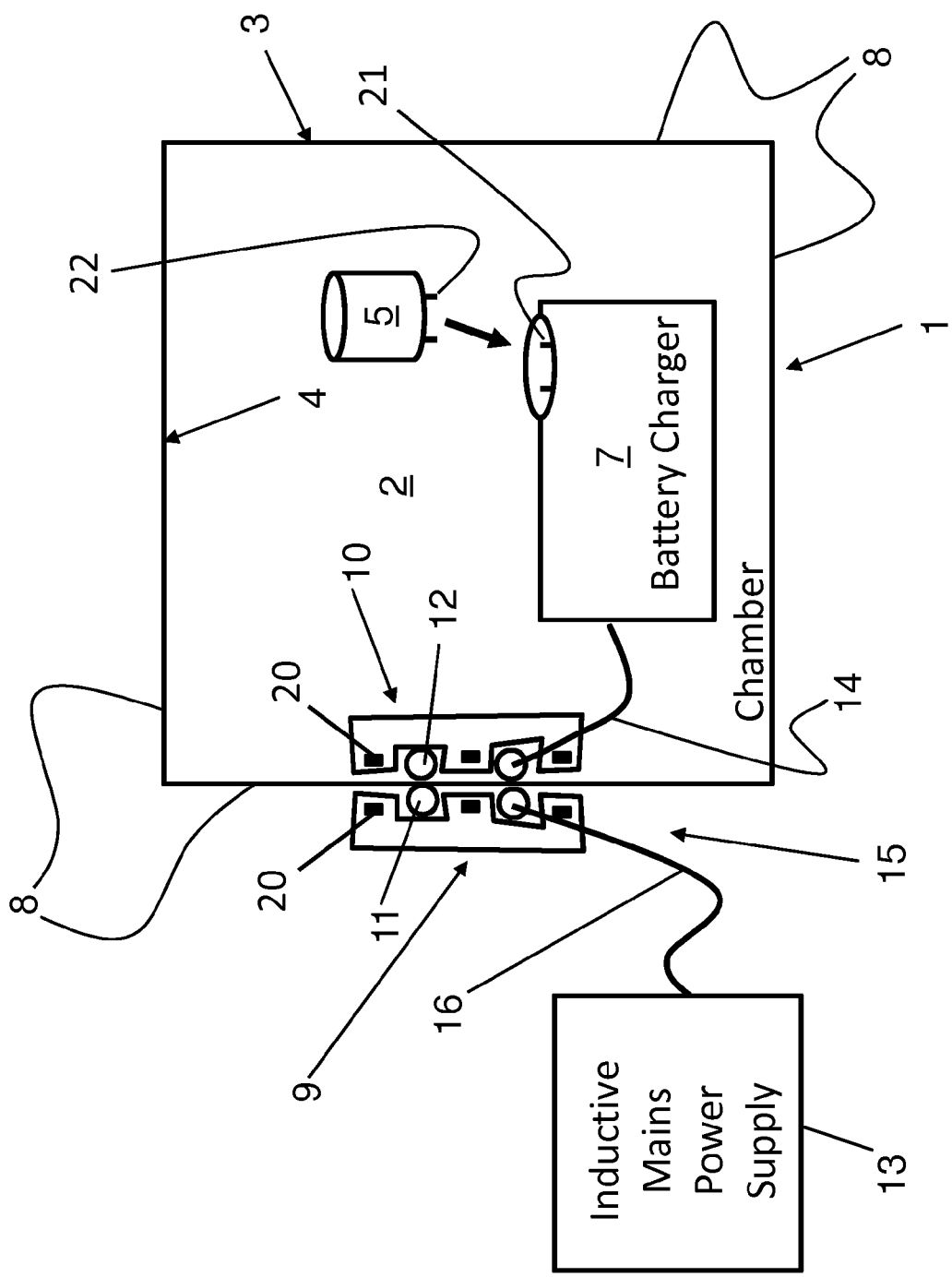
FIG. 1 is a block diagram of an exemplary embodiment of the sterilizer device according to the invention.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described.

It is contemplated that the device, system, and method of the present invention may be used to sterilize and recharge various types of batteries that may be used in a wide range of battery-powered surgical instruments or medical devices. In an exemplary embodiment, the device and method of the present invention is used to sterilize and recharge a removable and rechargeable battery of an endoscopic or laparoscopic surgical device.

Referring now to the figures of the drawings in detail and first, particularly to FIG. 1 thereof, there is shown an exemplary embodiment of the surgical sterilizer with an integrated battery charging device according to the present invention. The sterilization device 1 is comprised of a plurality of walls 8 that form a sealed enclosure 2 for the surgical sterilization of an object, such as a battery 5. Accordingly, the sterilization device 1 has an interior surface 4 and an exterior surface 3.

In this particular embodiment, the sterilization device 1 is non-magnetic, allows the transmission of electromagnetic waves through it, and is sealed such that it is impervious to one or more sterilizing components or agents. The components or agents for sterilizing the battery 5 may be built into or integral with the sterilization device 1 itself. Alternatively, the sterilization device 1 may be comprised of an already existing sterilization system that has been retrofitted with the battery recharging capability provided for by the device and method of the present invention.

To sterilize the battery 5, the sterilization device 1 may have, built in and integral therewith, one or more components or agents for sterilizing the battery. The one or more components or agents may utilize high temperature (>100° C.) or chemical agents, or a combination of both, in one or more vacuum, injection, washing, or ventilation cycles and/or phases. In general, the sterilization components or agents should be of a suitable type that does not short circuit the battery and is capable of permeating through a separate porous container that encloses the battery, if such a separate container is used as described detail below. For example, the sterilization device 1 may employ various autoclaving methods that use high-pressured steam, which are well known in the art. Alternatively, or in combination with the high temperature or high-pressured steam, various liquid and/or vapor chemical solutions, detergents, or disinfecting agents may be used. For example, ethylene oxide gas (EtO), hydrogen peroxide ($H_2O_2$), or peracetic acid can be used. In another example, a combination of hydrogen peroxide vapor ($H_2O_2$) and low-temperature (<100° C.) gas plasma can be used. The hydrogen peroxide acts as an oxidizing agent that affects sterilization by oxidation of key cellular components and is a highly effective bactericidal, virucidal, sporicidal, and fungicidal agent, even at low concentrations and temperatures. In yet another example, ultraviolet light or irradiation can be used to kill bacteria and other pathogens that may be present on the battery. It will be understood by those reasonably skilled in the art that a number of sterilization methods or techniques may be incorporated into the device, system, and method of the present invention and the specific sterilization methods or techniques described above are in no way intended as a limitation on the types of sterilizing methods or techniques that are contemplated by the device, system, and method of the present invention.

In an exemplary embodiment of the device and method of the present invention, the sterilization device 1 is comprised of any existing sterilizing system that employs a sealed enclosure 2. For example, there are existing sterilization systems that include a single or multi-tiered, sealed chamber that involves the combined use of hydrogen peroxide and low-temperature gas plasma for sterilizing a variety of single-channel flexible endoscopes, semi-rigid ureteroscopes and a wide range of other instruments. A series of sterilization systems made by Advanced Sterilization Products® (a Johnson & Johnson company) under the STERRAD® product name utilizes this technology. In another example, there are existing sterilization systems that include a chamber in which articles are placed in a racking system to be sterilized using vaporized hydrogen peroxide under vacuum conditions. The chamber is sealed using a silicone rubber gasket and a welded backhead, and utilizes an automatic door locking mechanism. An example of a sterilization system that utilizes this technology is made by the STERIS® Corporation under the product name, AMSCO® V-PRO 1 Low Temperature Sterilization System. In yet another example, other existing sterilization systems use one or more ethylene oxide (EtO) sterilant cartridges and are designed for use in sterilizing heat and moisture-sensitive materials that are unable to withstand the high temperature of conventional steam sterilization. These systems include a gasket-sealed chamber such that the entire sterilization cycle operates under a vacuum. An example of this type of system is the AMSCO® EAGLE® 3017 100% EO Sterilizer/Aerator, which is also made by the STERIS® Corporation.

Figure 3:
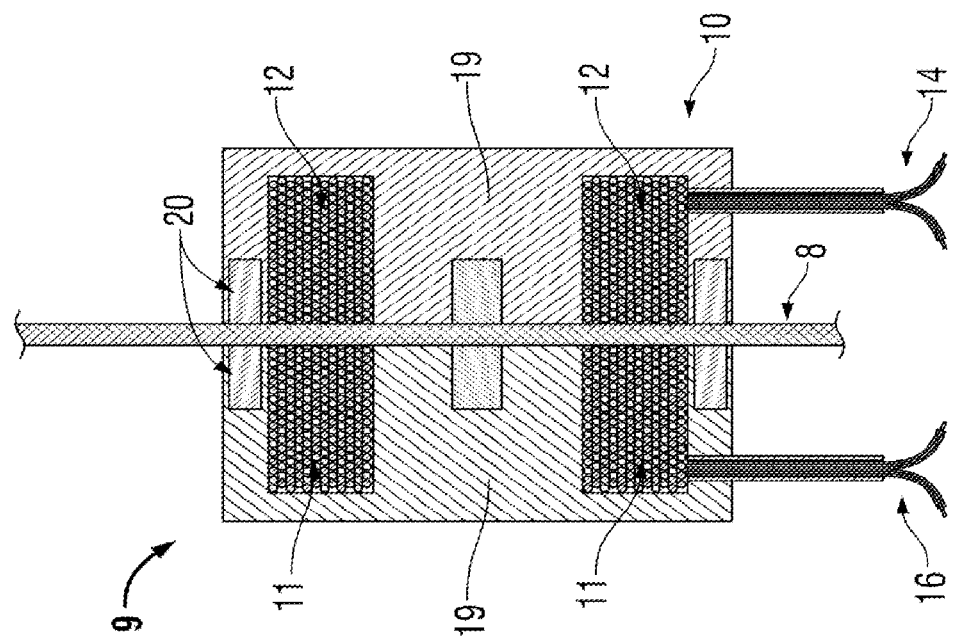
FIG. 3 is a fragmentary, side cross-sectional view of a wall of a sterilization chamber of the device of FIG. 1 having an exemplary embodiment of the inductive charging assembly applied thereon according to the present invention.
Figure 2:
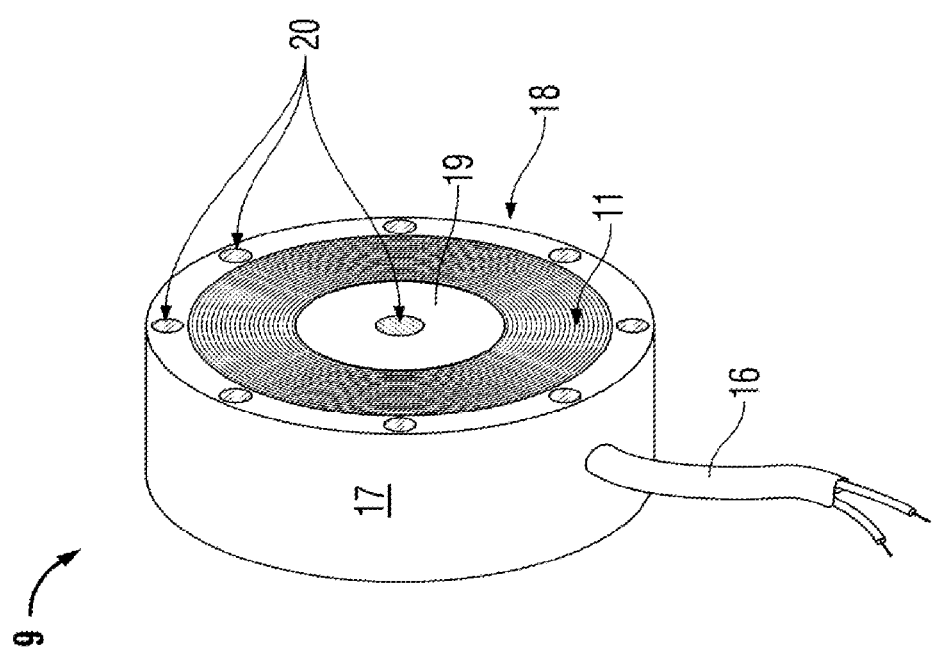
FIG. 2 is a fragmentary, perspective view of an exemplary embodiment of an inductive magnetic coil of the sterilizer device of FIG. 1.

Referring now to FIGS. 1-3, the recharging components used to recharge the battery 5 while the battery is being sterilized inside the sterilization enclosure 2 by the one or more sterilizing components or agents (not shown) are comprised of: (1) an inductive mains power supply 13, (2) an inductive charging assembly 15, and (3) a battery-charging platform 7 positioned inside the sealed enclosure 2 of the sterilization device 1. The battery-charging platform 7 has one or more electrical contacts 21 that come into direct contact with the electrical contacts 22 of battery 5 such that the battery is charged by the battery-charging platform 7 through conductive charging. In FIG. 1, the lines illustrating, diagrammatically, these respective electrical contact pairs 21 and 22 of the battery-charging platform 7 and the battery 5, are only exemplary and are not indicative of any particular conductive contacting configuration or a particular number of contacts.

To provide electrical current to the electrical contacts 21 of the battery-charging platform 7, the inductive mains power supply 13 and the inductive charging assembly 15 are used to supply the necessary electrical current across the sealed chamber wall 8 in such a way that does not breach the sterilization enclosure 2. In the exemplary embodiment shown in FIGS. 1-3, the inductive charging assembly 15 is comprised of an inductive power supply sub-assembly and an inductive power receiver sub-assembly, exemplary embodiments of each comprising a first magnetic inductive coil 9 and a second magnetic inductive coil 10. The first magnetic inductive coil 9 is a transmitter coil and has a primary winding 11. Similarly, the second magnetic inductive coil 10 is a power receiver or receiver coil and has a secondary winding 12. Each of the first and second magnetic inductive coils 9, 10 has a magnetic "pot" core (e.g., a ferrite core).

The first magnetic inductive coil 9 of the inductive charging assembly 15 is positioned at the exterior surface 3 of a wall 8 of the sterilization device 1 such that it is outside the sealed enclosure 2. Conversely, the second magnetic inductive coil 10 is positioned opposite the first magnetic inductive coil 9 at the interior surface 4 of the wall 8 of the sterilization device 1 such that it is inside the sealed enclosure 2. The first magnetic inductive coil 9 is electrically coupled to the inductive mains power supply 13 by a wired connection 16, such as a cord. The inductive mains power supply 13, located outside of the sterilization enclosure 2, is electrically coupled to an electrical mains (not shown). Due to the magnetic properties of the first and second magnetic inductive coils 9 and 10, the two coils are magnetically attracted to one another and, as a result, become substantially aligned across the wall 8 of the sterilization device 1 such that they are in close proximity to one another.

The first magnetic inductive coil 9, in connection with the inductive mains power supply 13, creates an electromagnetic field. The electromagnetic waves radiate from the first magnetic inductive coil 9 and induce an electrical current in the secondary winding 12 of the second magnetic inductive coil 10 across the wall 8 of the sterilization device 1. The electrical current that is induced in the second magnetic inductive coil 10 is thereafter conducted to the electrical contacts 21 of the battery-charging platform 7 using a wired connection 14, such as a cord. Accordingly, electrical power supplied from the outside of the sterilization enclosure 2 is conducted into the enclosure 2 for recharging the battery 5 without, at any point, breaching the walls 8 of the sterilization device 1.

Now, because the battery-charging platform 7 is positioned inside the sealed enclosure 2 of the sterilization device 1 so that the battery 5 may be recharged while simultaneously being sterilized, the battery-charging platform 7 and the one or more electrical contacts 21 contained therein must be comprised of materials that are suitable for use inside the sterilizing enclosure 2. In other words, the sterilizing components or agents cannot adversely affect the electrical or the structural integrity of the battery-charging platform 7 and/or the one or more electrical contacts 21 contained therein.

An exemplary embodiment of the first and second magnetic inductive coils 9 and 10 is shown in detail in FIGS. 2 and 3. Each coil 9, 10 is comprised of a circular housing 17 that has a hollow interior 18 and a spool-shaped column 19 that protrudes within the center of the housing 17. At least a portion of the housing 17 is comprised of a magnetic "pot" core. The primary and secondary windings 11 and 12 of the first and second magnetic inductive coils 9 and 10 are wound about the spool-shaped column 19 of the housings 17 in order to form the inductive portion of coils 9 and 10.

An aligning component 20, such as a plurality of compact magnets, is placed inside the hollow interior 18 of the housing 17 of each coil 9 and 10 such that the two coils are magnetically coupled to one another when placed opposite each other across the wall 8 of the sterilization device 1 as described above. The two coils 9 and 10 are also magnetically coupled to one another across the wall 8 by the magnetizing effects of the inductive coupling that is described above once an electrical current is applied. In FIGS. 2 and 3, the aligning component 20 is shown as a ring of equidistantly positioned magnets that surrounds a center magnet. This particular configuration is only one exemplary embodiment. Any aligning devices and methods can be used. For example, purely mechanical aligning devices are envisioned as well. Such a device could include an arc-shaped trough (not shown) in which the housings 17 may be removably placed.

In addition, the battery 5 may be placed inside a separate, sealed container (not shown) prior to placing the battery inside the sealed enclosure 2 of the sterilization device 1. The container may be comprised of a flexible bag or pouch or a rigid, semi-rigid or flexible box. In one embodiment, the container is comprised of materials that are suitable for use inside the sterilization enclosure 2 and are porous to the one or more sterilizing components or agents such that the one or more sterilizing components or agents penetrate the container and effectively sterilize the battery 5. At the same time, the materials comprising the container must also be impervious to microbial contaminants so as to form a microbial seal around the battery 5. This microbial seal ensures that there is no cross-contamination between the electrical contacts 22 of the battery and the one or more electrical contacts 21 of the battery-charging platform 7 in circumstances where the sterilization components or agents cannot effectively reach the areas of the respective electrical contacts 22 and 21 while the battery 5 and the battery-charging platform 7 are in physical contact with one another. Also, the container is comprised of a sufficiently conductive material or, has its own electrical contacts, such that the one or more electrical contacts 22 of the battery may be sealed inside the container and still receive the electrical current flowing from the electrical contacts 21 of the battery-charging platform 7. Examples of such containers include Mylar® pouches and polypropylene wraps. Alternatively, a peel-back, molded, hard plastic component may be applied to the electrical contacts 22 of the battery to form a microbial seal just at the contacts to prevent the occurrence of cross-contamination as described above.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A device for sterilizing and charging a battery of an instrument, comprising:
    a sterilization device:
        sealingly enclosing therein at least one battery of an instrument; and
        operable to sterilize the at least one battery;
    an inductively powered battery-charging device disposed inside the sterilization device and having:
        a charger operable to be placed in conductive contact with and charge the at least one battery; and
        a power receiver sub-assembly electrically coupled to the charger and operable to:
            receive electrical power inductively from outside the sterilization device; and
            supply the received electrical power to the charger to charge the battery during sterilization; and
    a power supply disposed outside the sterilization device and operable to supply power inductively to the power receiver sub-assembly through the sterilization device.

2. The device according to claim 1, wherein the charger includes at least one electrical contact shaped to conductively contact at least one corresponding electrical battery contact of the battery.

3. The device according to claim 1, wherein:
    the power supply has:
        an inductive power supply sub-assembly; and
        an electric mains supply operable to supply power to the inductive power supply sub-assembly; and
    the inductive power supply sub-assembly and the power receiver sub-assembly together form an inductive charging assembly.

4. The device according to claim 3, wherein:
    the inductive power supply sub-assembly is comprised of a first magnetic inductive coil disposed outside the sterilization device and having a primary winding electrically coupled to the electric mains supply; and
    the power receiver sub-assembly is comprised of a second magnetic inductive coil disposed within the sterilization device and having a secondary winding electrically coupled to the charger, the second magnetic inductive coil being adjacent to and substantially aligned with the first magnetic inductive coil such that the first magnetic inductive coil induces an electrical current in the second magnetic inductive coil when the electric mains supply powers the first magnetic inductive coil.

5. The device according to claim 3, wherein the inductive charging assembly does not breach the sterilization device.

6. The device according to claim 1, wherein the sterilization device is comprised of a material that permits transmission of electromagnetic waves therethrough.

7. The device according to claim 1, wherein the sterilization device is operable to surgically sterilize the at least one battery using at least one of:
  temperature of at least 100 degrees Celsius;
  a chemical agent; and
  radiation.

8. The device according to claim 4, wherein the first and second magnetic inductive coils each have a magnetic core.

9. The device according to claim 8, wherein the first and second magnetic inductive coils each have a ferrite core.

10. The device according to claim 4, further comprising an alignment component operable to substantially align the first and second magnetic inductive coils on either side of the sterilization device.

11. The device according to claim 10, wherein the alignment component is comprised of at least one first magnet of the first magnetic inductive coil and at least one second magnet of the second magnetic inductive coil having magnetically opposite poles.

12. The device according to claim 1, further comprising a sealed container operable:
  to enclose the at least one battery to create a microbial seal around the at least one battery; and
  to permit charging of the at least one battery while enclosing the at least one battery in the microbial seal.

13. A device for sterilizing and charging a battery of an instrument, comprising:
  a sterilization device:
    sealingly enclosing therein at least one battery of an instrument; and
    operable to sterilize the at least one battery;
  an inductively powered battery-charging device disposed inside the sterilization device and having:
    a charger operable to be placed in conductive contact with and charge the at least one battery; and
    a power receiver sub-assembly electrically coupled to the charger and operable to:
      receive electrical power inductively from outside the sterilization device; and
      supply the received electrical power to the charger to charge the battery during sterilization;
  a power supply disposed outside the sterilization device and having:
    an inductive power supply sub-assembly operable to supply power inductively to the power receiver sub-assembly through the sterilization device; and
    an electric mains supply operable to supply power to the inductive power supply sub-assembly; and
  the inductive power supply sub-assembly and the power receiver sub-assembly together forming an inductive charging assembly.

14. The device according to claim 13, wherein the charger includes at least one electrical contact shaped to conductively contact at least one corresponding electrical battery contact of the battery.

15. The device according to claim 13, wherein:
  the inductive power supply sub-assembly is comprised of a first magnetic inductive coil disposed outside the sterilization device and having a primary winding electrically coupled to the electric mains supply; and
  the power receiver sub-assembly is comprised of a second magnetic inductive coil disposed within the sterilization device and having a secondary winding electrically coupled to the charger, the second magnetic inductive coil being adjacent to and substantially aligned with the first magnetic inductive coil such that the first magnetic inductive coil induces an electrical current in the second magnetic inductive coil when the electric mains supply powers the first magnetic inductive coil.

16. The device according to claim 13, wherein the inductive charging assembly does not breach the sterilization device.

17. The device according to claim 13, wherein the sterilization device is comprised of a material that permits transmission of electromagnetic waves therethrough.

18. A device for sterilizing and charging a battery of an instrument, comprising:
  a sterilization device sealingly enclosing therein at least one battery of an instrument and operable to sterilize the at least one battery; and
  an inductively powered battery-charging device:
    disposed inside the sterilization device and in conductive contact with the at least one battery such that it is operable to charge the battery during sterilization; and
    operable to inductively receive power from a power source located outside of the sterilization device such that the sterilization device is not breached.

* * * * *